United States Patent [19]

Zhou et al.

[11] Patent Number: 6,120,531
[45] Date of Patent: Sep. 19, 2000

[54] PHYSIOTHERAPY FIBER, SHOES, FABRIC, AND CLOTHES UTILIZING ELECTROMAGNETIC ENERGY

[75] Inventors: Lin Zhou; Xue-Shan Zhang, both of Towaco, N.J.

[73] Assignee: Micron, Technology, Boise, Id.

[21] Appl. No.: 08/954,346

[22] Filed: Oct. 17, 1997

Related U.S. Application Data

[63] Continuation-in-part of application No. 08/557,207, Nov. 14, 1995, abandoned, which is a continuation-in-part of application No. 08/374,475, Jan. 17, 1995, abandoned, which is a continuation-in-part of application No. 08/395,042, Feb. 28, 1995, Pat. No. 5,814,078, which is a division of application No. 07/827,636, Jan. 29, 1992, abandoned, which is a continuation-in-part of application No. 07/508,302, Apr. 12, 1990, abandoned, which is a continuation-in-part of application No. 07/103,603, Oct. 1, 1987, abandoned.

[51] Int. Cl.$^7$ .................................................. A61N 5/06
[52] U.S. Cl. ............................... 607/111; 600/15; 607/1; 607/100; 442/131; 442/229; 442/377
[58] Field of Search ................... 607/1, 2, 3, 44, 607/45, 46, 50, 96, 100, 108, 111, 144, 149; 600/372, 382, 384, 386, 9, 15, 26; 606/32, 33, 41; 442/131, 132, 133, 228, 229, 376, 377

[56] References Cited

U.S. PATENT DOCUMENTS

| 187,105 | 2/1877 | Craw ........................................ 607/144 |
| 194,184 | 8/1877 | Smith et al. ............................. 607/144 |
| 743,306 | 11/1903 | Merwin ..................................... 604/20 |
| 1,429,443 | 9/1922 | McFaddin ............................... 128/395 |
| 2,494,987 | 9/1950 | Chaitin ..................................... 607/108 |
| 3,658,068 | 4/1972 | McNall ..................................... 128/395 |
| 3,773,049 | 11/1973 | Rabichev et al. .......................... 607/1 |
| 3,818,914 | 6/1974 | Bender ..................................... 128/396 |
| 3,821,576 | 6/1974 | Larson ..................................... 128/395 |
| 3,890,530 | 6/1975 | Hammer et al. ........................ 313/489 |
| 3,946,193 | 3/1976 | Giese ....................................... 607/111 |
| 3,967,153 | 6/1976 | Milke et al. ............................. 313/492 |
| 3,995,191 | 11/1976 | Kaduk et al. ............................ 313/489 |
| 4,234,907 | 11/1980 | Daniel ....................................... 362/32 |

(List continued on next page.)

FOREIGN PATENT DOCUMENTS

| 85100593 | 6/1986 | China . |
| 1157584 | 5/1958 | France ................................... 128/395 |
| 3027516 | 2/1982 | Germany .............................. 128/395 |
| 3823178 | 1/1990 | Germany .................................... 607/1 |
| 2135582 | 9/1984 | United Kingdom ....................... 607/1 |

OTHER PUBLICATIONS

Health Dept. of Yunnan, China "Certificate of the clinical application and basic scientific research WS–Freq Spect. App.," Jun. 1983.

"Notice of Judgement under the FDA," 11–1951, p. 467, 128/395, Federal Register.

"Luminescence of Alkaline–Earth Pyrophosphates, Activated with Divalent Europium, "–1968, Wanmaker et al., 128/395.

"Certificate of the Clinical Application and Basic Scientific Research W5–Freq. Spect. App., "6–1983, Health Department of Yunnan, China.

*Primary Examiner*—William E. Kamm
*Assistant Examiner*—Kennedy J. Schaetzle
*Attorney, Agent, or Firm*—Workman, Nydegger & Seeley

[57] ABSTRACT

Fiber, fabric, clothes, and shoes having a material incorporated therein which, when stimulated by energy, emits a predetermined spectrum having a first electromagnetic radiation having a wavelength range selected from the group consisting of about 0.2 μm to about 50 μm, and about 0.4 μm to about 25 μm, and a second radiation having a wavelength range selected from the group consisting of about 7500 μm to about 100,000 μm, and about 5400 μm to about 500,000 μm, similar to radiation generated by the human body over similar ranges. A reflecting layer is adjacent to a fabric having the material incorporated therein such that body heat is conserved so as to achieve a therapeutic result. The energy stimulating the material can be body heat, electrical heat, magnetic energy, or other energy forms.

26 Claims, 10 Drawing Sheets

U.S. PATENT DOCUMENTS

| | | | |
|---|---|---|---|
| 4,287,554 | 9/1981 | Wolff | 362/218 |
| 4,420,709 | 12/1983 | Rattray | 313/487 |
| 4,505,545 | 3/1985 | Salia-Munoz | 350/321 |
| 4,540,915 | 9/1985 | Shinkai et al. | 313/486 |
| 4,558,700 | 12/1985 | Mutzhus | 128/395 |
| 4,601,917 | 7/1986 | Russo et al. | 106/287.19 |
| 4,607,191 | 8/1986 | Flaherty | 313/486 |
| 4,663,563 | 5/1987 | Taya et al. | 313/487 |
| 4,680,822 | 7/1987 | Fujino et al. | 607/96 |
| 4,716,337 | 12/1987 | Huiskes et al. | 313/487 |
| 4,762,131 | 8/1988 | Okuda | 128/395 |
| 5,106,657 | 4/1992 | Isshiki | 428/375 |
| 5,226,020 | 7/1993 | Li et al. | 600/9 |
| 5,425,975 | 6/1995 | Koiso et al. | 607/96 |

1. ENERGY SOURCE
2. SIMULATED BIO-SPECTRUM GENERATOR
3. ENERGY TRANSDUCER
4. SIMULATED BIO-SPECTRUM GENERATING COMPONENT

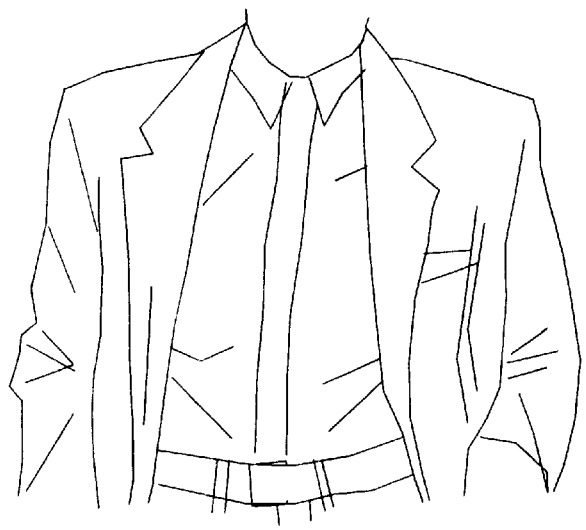 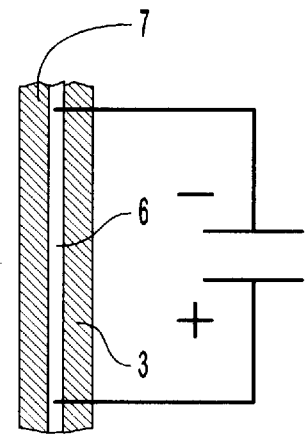
FIG. 9A  FIG. 9B
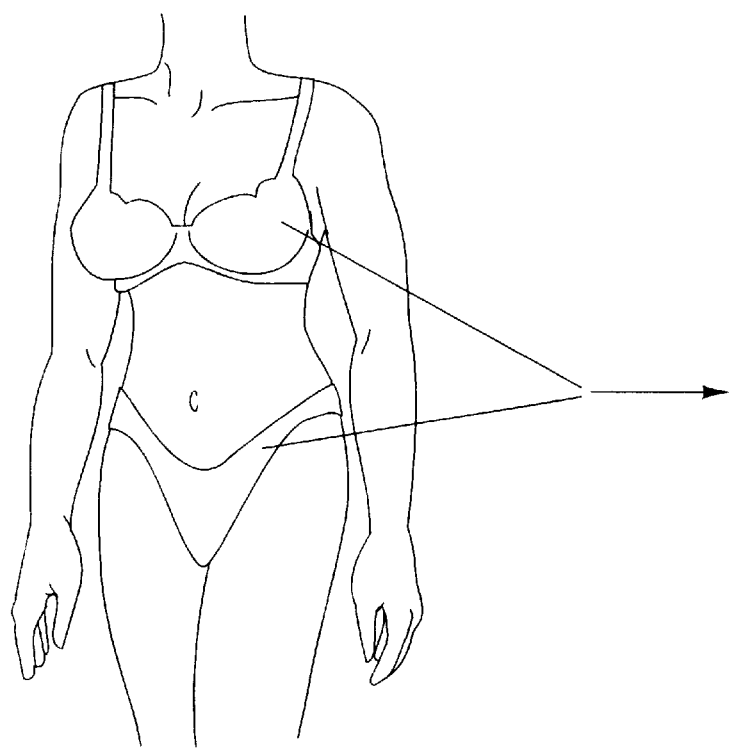 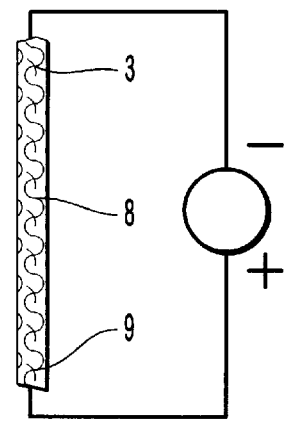
FIG. 10A  FIG. 10B

PHYSIOTHERAPY FIBER, SHOES, FABRIC, AND CLOTHES UTILIZING ELECTROMAGNETIC ENERGY

RELATED APPLICATIONS

This application is a continuation-in-part application of U.S. patent application Ser. No. 08/557,207 that was filed on Nov. 14, 1995, now U.S. Pat. No. 5,792,184, which is a continuation-in-part application of both U.S. patent application Ser. No. 08/374,475 that was filed on Jan. 17, 1995, abandoned, and U.S. patent application Ser. No. 08/395,042 that was filed on Feb. 28, 1995, now, U.S. Pat. No. 5,814,078, which is a divisional of U.S. patent application Ser. No. 07/827,636 that was filed on Jan. 29, 1992, abandoned, which is a continuation-in-part of U.S. patent application Ser. No. 07/508,302 that was filed on Apr. 12, 1990, which is a continuation-in-part of U.S. patent application Ser. No. 07/103,808 that was filed on Oct. 1, 1987, and claims priority to P.R.C. Patent Applications 87,103,603 and 87,208,158, both filed on May 20, 1987, abandoned, each of the foregoing U.S. Applications being incorporated herein by reference.

BACKGROUND OF THE INVENTION

1. The Field of the Invention

The present application is related to the physiotherapy field and is more particularly related to physiotherapy fibers, fabric, shoes, and clothing.

2. The Relevant Technology

FIG. 1A is a graph of a measured electromagnetic radiation that was emitted from a human body, where the measured radiation is in a range from about 1 $\mu$m to about 16 $\mu$m. Over a broader spectrum, electromagnetic radiation that is emitted from a human body is shown in the graph in FIG. 2 as indicated by the dotted and dashed line. As seen in FIG. 2, the human body emits a first radiation that extends in a wavelength range from about 0.2 $\mu$m to about 50 $\mu$m and a second radiation that extends in a wavelength range from about 7500 $\mu$m to about 100,000 $\mu$m. It is also seen in FIG. 2 that there is substantially no radiation that extends in a wavelength range from about 50 $\mu$m to about 100,000 $\mu$m. FIG. 2 also shows that there is substantially no radiation that extends in a wavelength range from about 25 $\mu$m to about 5400 $\mu$m. A further interpretation of FIG. 2 is that there is a first radiation that extends over a wavelength range from about 0.4 $\mu$m to about 25 $\mu$m and a second radiation that extends over a wavelength range from about 5400 $\mu$m to about 500,000 $\mu$m.

FIG. 3 shows a graph of electromagnetic radiation emitted from a heat lamp As seen in FIG. 3, electromagnetic radiation extends in a wavelength range from about 0.0.5 $\mu$m to about 3.5 $\mu$m. The heat lamp is produced by Phillips Electronics as their Model No. HP3690. The radiation from the depicted heat lamp differs significantly over the same range from that of the human body, by comparison to FIGS. 1A and 2.

FIG. 4 shows spectrum produced by conventional electromagnetic radiation devices in the ranges of 0.72 $\mu$m to 2 $\mu$m and 0.72 $\mu$m to 50 $\mu$m, each of which differs significantly from the electromagnetic spectrum emitted from the human body.

FIG. 5 shows, at letters A and C, electromagnetic radiation at an 8 mm wavelength that was emitted from the heat lamp of FIG. 3 and a chest of a human body, respectively. In each case, the instrument measuring electromagnetic radiation at an 8 mm wavelength was separated by a distance of 1.5 meters from the heat lamp and the chest of the human body. The measurement was taken from the heat lamp while ambient temperature was about 115° C. and while the emitter of the heat lamp had a temperature of 1723° C., where the emitter has a 1.7 $\mu$m maximum wavelength. The measurement of the human body was taken in an ambient temperature of about 29° C. FIG. 5, at letters A and C, shows that radiation from the human body is significantly higher than that of the heat lamp at 8 mm.

Shoes and clothes that improve health and keep the body warm and comfortable have always been a target goal of physiotherapy sciences and industries. The appearance in the market of shoes associated with advertising that advocates healthy feet by virtue of the structure thereof, and of pads for the inside of the shoe which can prevent foot odor, are examples. The prior art does not teach clothing made of a fabric which conserves body heat, and when stimulated by energy, emits an electromagnetic radiation that is similar to that created by the human body as seen in FIGS. 1A, 2, and 5C.

SUMMARY OF THE INVENTION

The invention provides fiber, fabric, clothes, and shoes that have a therapeutic effect. As determined by the science of spectroscopy, a variety of chemical substances can be formed which, when stimulated by energy, such as heat or electricity, emits a predetermined radiation. By using the science of spectroscopy, a variety of materials or chemical substances can be formed, which when stimulated by energy emit the predetermined radiation of the human body as seen in FIGS. 1A, 2, and 5C. Such a chemical substance can be incorporated into a fabric from which an article of clothing is manufactured. Body heat, with or without an external supply of energy such as from a battery source, is then used as the energy to stimulate the chemical substance to emit a predetermined radiation. Preferably, the predetermined radiation is a first radiation extending in wavelength range from about 0.2 $\mu$m to about 50 $\mu$m and a second radiation extending in wavelength range from about 7500 $\mu$m to about 100,000 $\mu$m. More preferably, the predetermined radiation is a first radiation extending in wavelength range from about 0.4 $\mu$m to about 25 $\mu$m and a second radiation extending in wavelength range from about 5400 $\mu$m to about 500,000 $\mu$m.

The chemical substance is preferably a metal oxide which, in addition to emitting the foregoing radiation wavelength ranges, also reflects heat back into the body as the clothing are worn. The fabric can be used to form a lining in a garment such as a shirt, foundation garment, or shoes. While the process is not fully understood, it is believed that a therapeutic result is achieved by the radiation of the body with the foregoing radiation wavelengths, and also in that the body maintains warmth through the conservation of body heat by the reflection of heat back into the body. Additional components of heat are also conserved when an external power supply, such as a battery source is used for electrical resistance heating.

In the case of shoes, the chemical substance is incorporated into a fabric on an interior lining of the shoe, such as in the sole and upper portion of the shoe. The lining serves to reflect body heat back into the foot. In the case of other clothes, such as a foundation garment, shirt, hat, pants, sweater, belt, socks, gloves, cap, and other similar clothes, the chemical substance can be incorporated into the fabric making up the clothes by applying the same to surfaces of the fibers that make up the fabric.

These and other features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the following drawings:

FIGS. 7A-1, 7A-2, 7B-1, 7B-2, 7C-1, 7C-2 and 7D diagrammatically illustrate embodiments of a body through which energy is propagated to stimulate a material incorporated therein so as to emit from said material a predetermined radiation;

FIGS. 9A and 9B depict examples of a jacket and fabric of the jacket, respectively, where the fabric has a material incorporated therein that conserves body heat, and when the material is stimulated by energy, the material emits a predetermined radiation;

FIGS. 10A and 10B depict examples of foundation garments and fabric therefrom, respectively, where the fabric has a material incorporated therein that conserves body heat, and when that material is stimulated by energy, the material emits a predetermined radiation;

DETAILED DESCRIPTION OF THE PREFERRED EMBODIMENTS

Figure 1A:
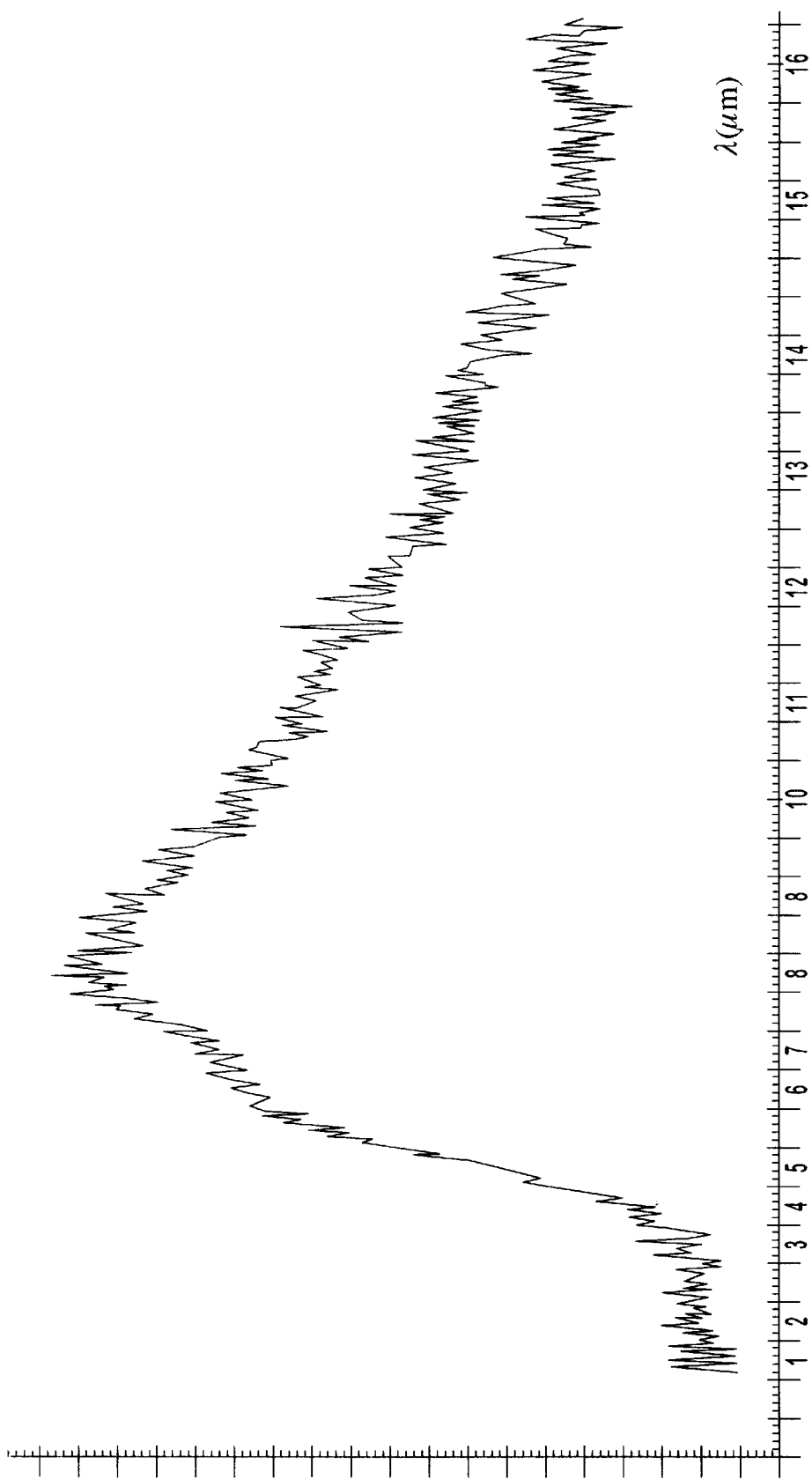
FIG. 1A is a graph of intensity versus wavelength, showing, for a limited range, electromagnetic radiation emitted from a human body.
Figure 1B:
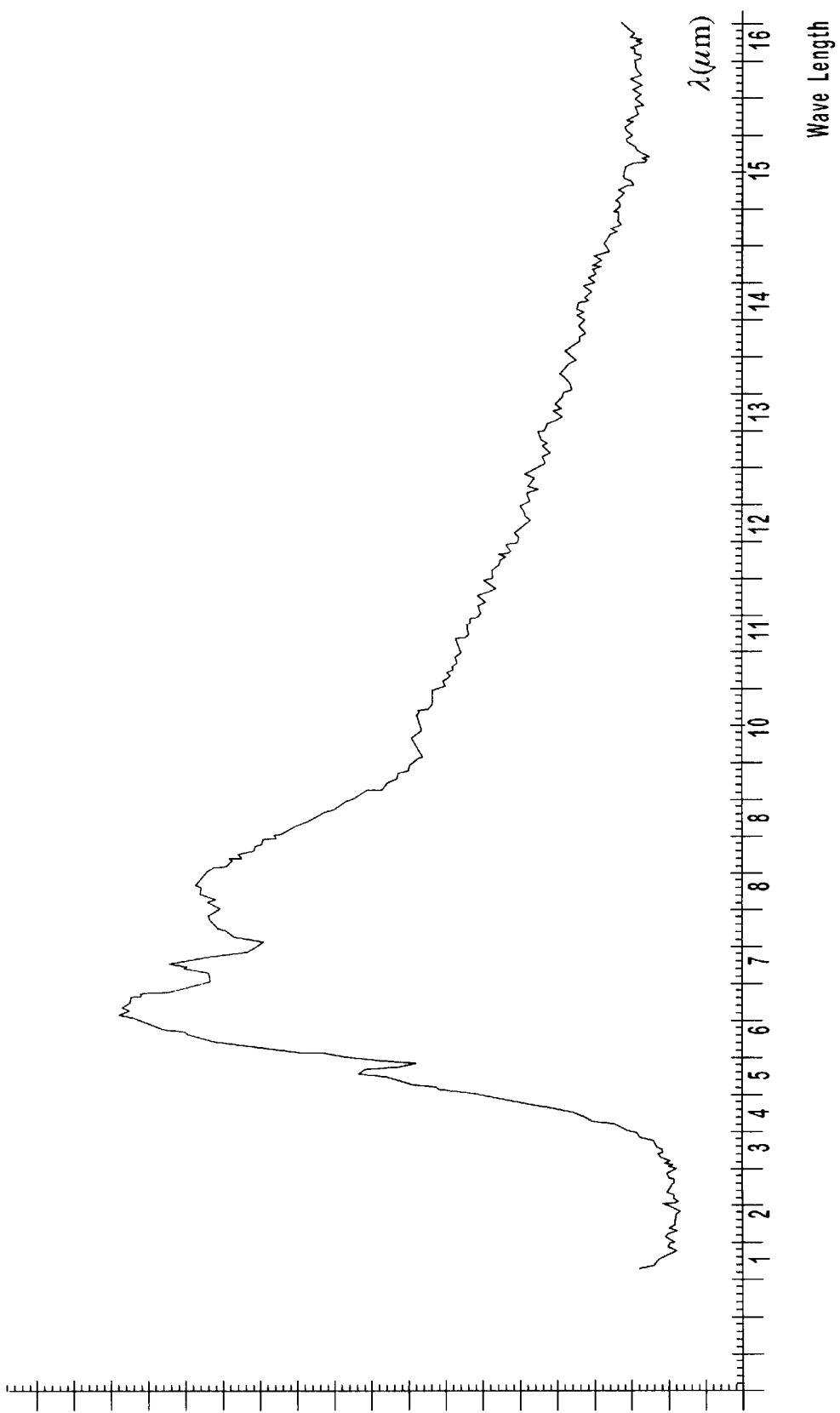
FIG. 1B is a graph of intensity versus wavelength, showing, for a limited range, electromagnetic radiation emitted by a material that is stimulated by energy.

FIG. 1B is a graph of a measured electromagnetic radiation that was emitted from a material that was stimulated by energy. The measured radiation seen in FIG. 1B extends in a wavelength range from about 1 $\mu$m to about 16 $\mu$m. This radiation is closer in the range of spectrum to the human body, as seen in FIG. 1A than is the radiation emitted by the heat lamp as shown in FIG. 3.

Figure 2:
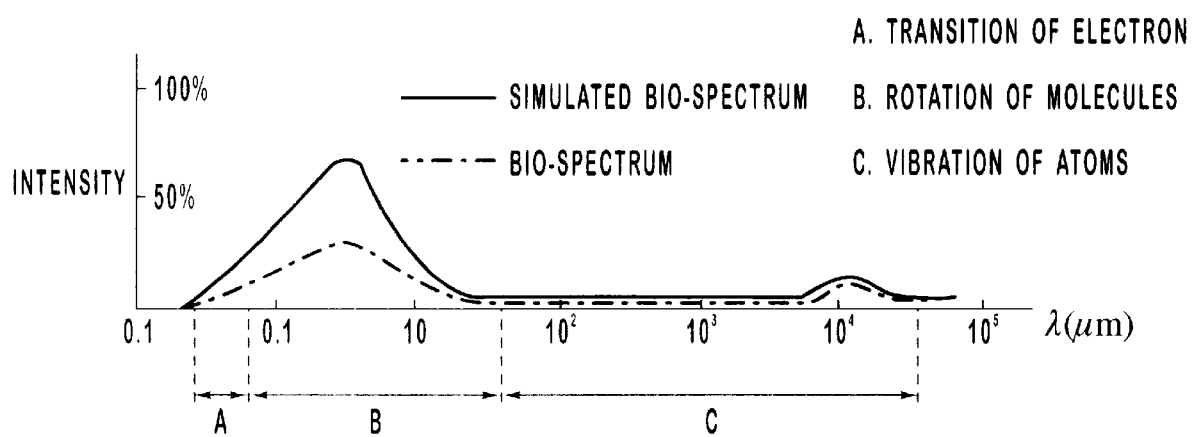
FIG. 2 is a graph of intensity versus wavelength, the graph showing in a dotted and dashed electromagnetic radiation emitted from a human body, and at an unbroken line showing of electromagnetic radiation emitted from a material useful in the present invention that is stimulated by energy.
Figure 3:
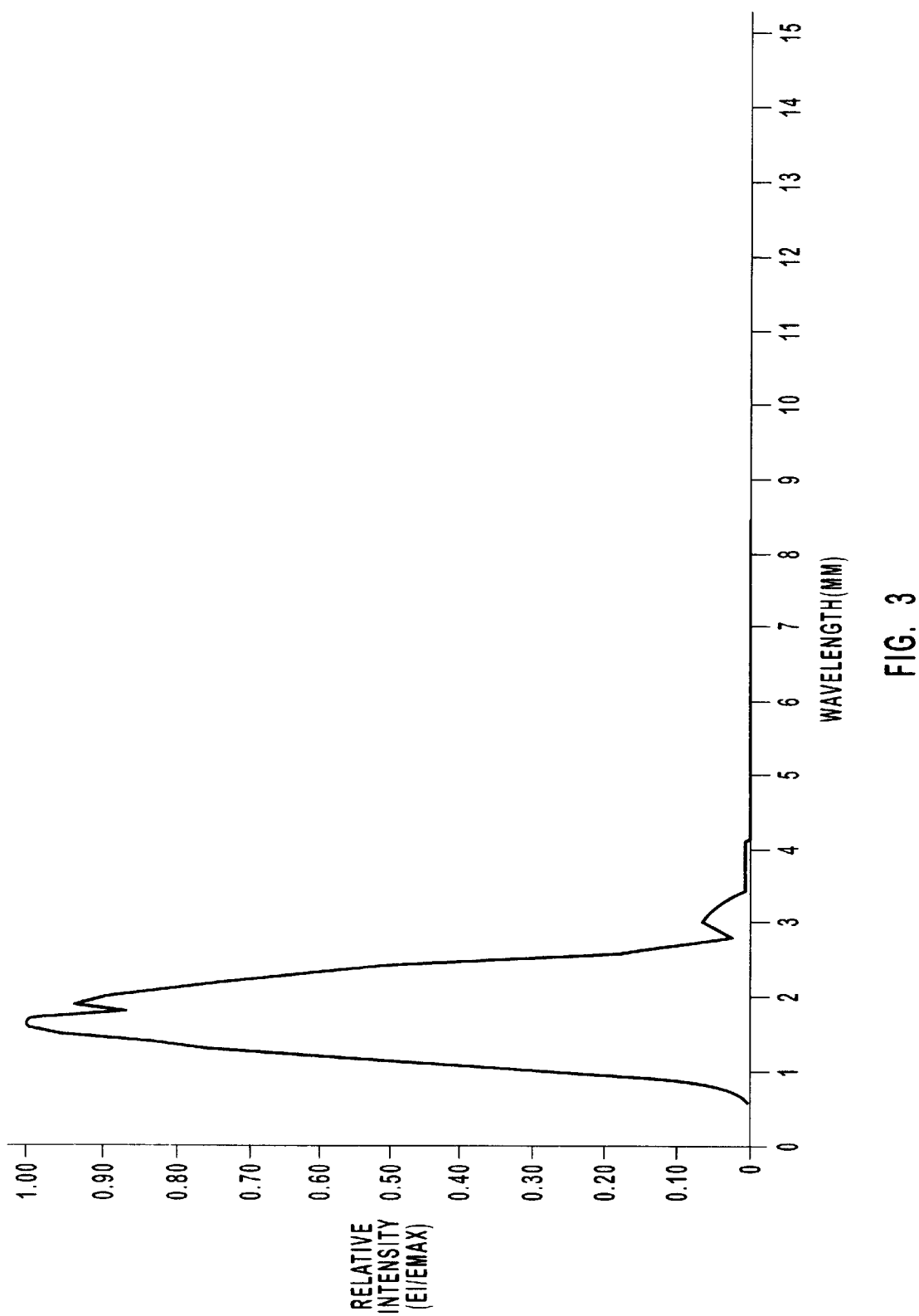
FIG. 3 shows a graph of intensity versus wavelength for electromagnetic radiation emitted from a heat lamp.
Figure 4:
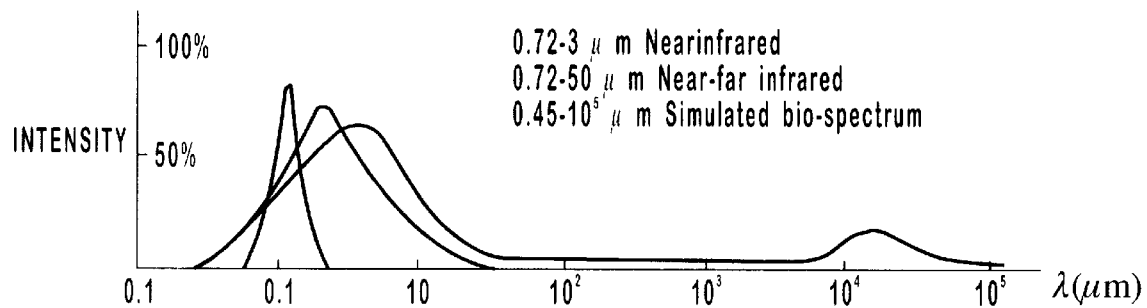
FIG. 4 shows a graph of intensity versus wavelength produced by conventional electromagnetic radiation devices and by a material useful in the present invention that is stimulated by energy.
Figure 5:
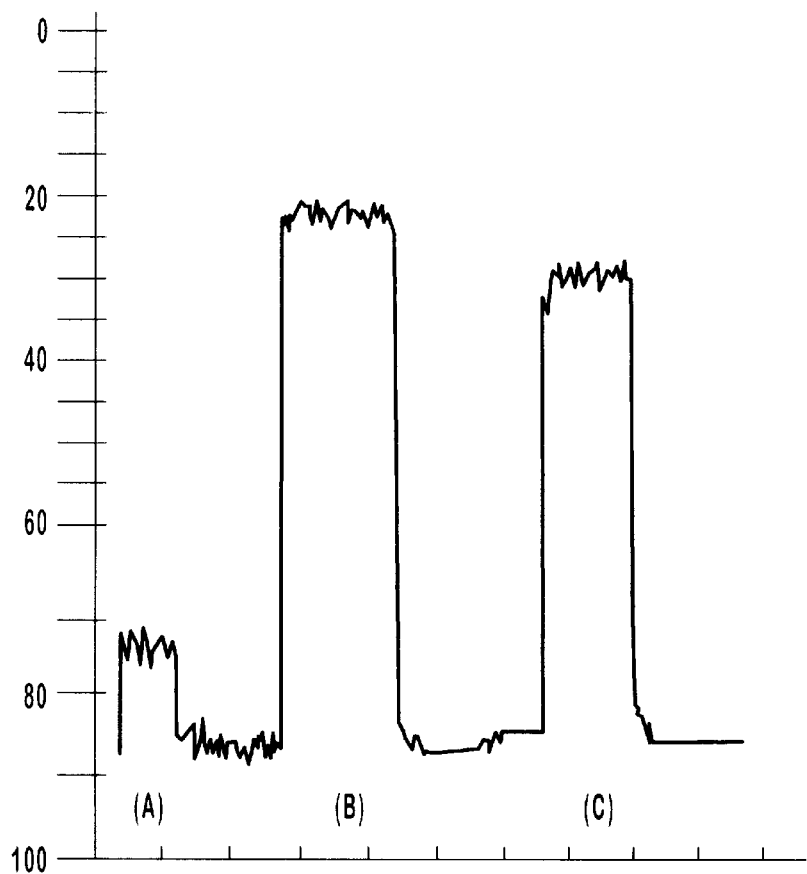
FIG. 5 shows a graph of intensity versus time for electromagnetic radiation at an 8 mm wavelength that was emitted, at reference A by the heat lamp of FIG. 3, at reference B by a material useful in the present invention that is stimulated by energy, and at letter C by a chest of a human body.

FIG. 5 shows 8 mm wavelength electromagnetic radiation that was emitted by the heat lamp of FIG. 3 at letter A, by a material useful in the present invention that is stimulated by energy at letter B, and by a chest of a human body at letter C. FIG. 5 shows that, by comparison, little energy is emitted at 8 mm from the heat lamp, whereas a similar amount of radiation is emitted by the material useful in the present invention at reference B and by the chest of the human body at reference C. The 8 mm wavelength electromagnetic radiation is also seen by comparison in the graph in FIG. 2, where the radiation from the human body is indicated by the dotted and dashed line and radiation from a material useful in the present invention is indicated by a solid line. From FIGS. 1 through 5, it can be seen that materials can be derived, which when stimulated by energy, will produce an electromagnetic spectrum having a wavelength range similar to that of the human body. It can also be seen that not all materials that are stimulated by an energy will produce an electromagnetic spectrum having a wavelength range that is similar to that of the human body, such as the material stimulated by electricity that is in use in the heat lamp for which a spectrum is depicted in FIGS. 3 and 5A, or materials from which spectrum is generated in FIG. 4 in the ranges of 0.72 $\mu$m to 2 $\mu$m and 0.72 $\mu$m to 50 $\mu$m, each of which differs significantly from the electromagnetic spectrum emitted from the human body.

Figure 6:
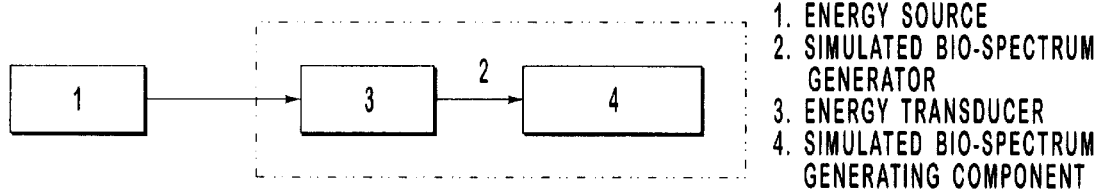
FIG. 6 is a block diagram depicting the process for using energy to stimulate a material that will in turn emit a predetermined radiation.

FIG. 6 is a block diagram depicting the process for using an energy source 1 to stimulate a material 4 that will in turn emit a predetermined radiation, where 3 represents an energy transducer. The reference 2 in FIG. 6 can be a fabric into which material 4 is incorporated. Energy source 1 can be of many forms, such as thermal energy such as body heat, electrical energy, magnetic energy, solar energy, chemical energy, or biological energy, etc. In the case of shoes and clothes having fabric 2 with material 4 incorporated therein, electrical energy and body heat are preferable because it is readily available. Electrical energy can be supplied by an AC power source, or by a battery. Magnetic energy can be supplied by a magnet structure.

Energy source 1 is transduced into thermal or magnetic energy by energy transducer 2 to provide energy to material 4. Material 4 can be composed of monomer or compounds of one or more chemical elements in the periodic table. Upon excitation by energy, the transitions of energy levels of the elements or compounds are emitted in the form of electromagnetic radiation. Material 4 will preferably be composed of a substance which, when stimulated by energy source 1, emits a first radiation having a wavelength range extending from about 0.2 $\mu$m to about 50 $\mu$m and a second radiation having a wavelength range extending from about 7500 $\mu$m to about 100,000 $\mu$m. It is also desirable to use a substance which, when stimulated by energy source 1, emits a first radiation having a wavelength range extending from about 0.4 μm to about 25 μm and a second radiation having a wavelength range extending from about 5400 μm to about 500,000 μm (the first and second radiations being referred to hereinafter as "Simulated Bio-spectrum").

While the physiological mechanism is not fully understood, the inventors believe that when the electromagnetic radiation from material 4, over a particular range, matches with an absorption band of a human body, a large portion of the radiant energy carried by the electromagnetic radiation is absorbed, causing changes of the energies of molecules, atoms, or electrons in human body, which then elicits oscillation, and provides a therapeutic effect.

The selection of a material which, when stimulated by energy produces the Simulated Bio-spectrum, is selected in accordance with the following principles:

a. The spectrum of irradiation of the chemical elements after acquiring energy should be distributed as widely as possible between the micrometer band and the millimeter band. If the irradiation is only in the micrometer (infrared) band or only in the millimeter band, the biological effects produced are not good enough. In order to make the produced biological effects favorable to the growth and development of living organisms, radiant signals should be present all over the range from micrometers to millimeters. Therefore, a broad spectrum of μm-mm is a distinct feature of the present invention. Selection and proportion of the chemical elements are indispensable to the realization of the broad frequency spectrum and are based on the fact that the elements must be able to generate the Simulated Bio-spectrum when excited by energy. As those of skill in the science of spectroscopy will appreciate, a wide variety of chemicals can be used to produce this spectrum.

b. The elements should be technically as similar to the chemical constituents of the bio-substances in living organism as possible. The frequency distribution of the inherent bio-spectrum of living organism, for example as seen in FIGS. 1A, 2, and 5C, is then considered.

The selected material can be stimulated by a variety of energy sources to produce the Simulated Bio-spectrums. These different sources of energy are now described.

1. Electricity as Energy Source.

Electric wires of certain resistance are embedded into plastics or textiles that contain the Simulated Bio-spectrum generating substances. The electric wires are designed to have certain heat generating power and cross sectional area like that used in an electric heating blanket. When being heated by electricity, this kind of plastic or textile can generate a Simulated Bio-spectrum of certain intensity, which, it is believed, can enhance body fluid circulation and improve the function of the nervous system. It is beneficial to health when used for a long time. This kind of material can be made into electric heating blankets, local health bands, chair cushions for offices, cars, boats, or airplanes, mattresses, beds for home use, and sporting goods. The heating temperature is controlled below 45° C.

2. Magnetic field as energy source.

Magnetic material can be added into the plastic or textile containing substances that generate the simulated bio-spectrum. The magnetic material can be various kinds of permanent magnets. Under the action of the magnetic field, the simulated bio-spectrum generated by the plastic or textile can be intensified. The dual action of the spectrum and magnetic field can enhance body fluid circulation and health care. This example can be used to make various kinds of mattresses or chair cushions, hats, and shoes, waist or knee bands, or to wrap strong magnetic materials to make various kinds of magneto-spectral health caring equipment.

3. Solar energy as heating source.

Plastics or textiles, including plastic membranes, containing the simulated bio-spectrum generating substances can be used to make large tents or rooms so that the plastics or textiles can be heated by solar energy and become the simulated bio-spectrum generator. This example can be used for seedling nursing, breeding, or low temperature culture.

4. Body heat or Ambient Heat As Energy Source.

The plastics or textiles containing simulated bio-spectrum generating substances can be used to make articles for daily use such as shoes, caps, waist bands, mattresses or cushions, so that heat produced by human body or natural heat of the environment can act as the energy source. Long term contact with such articles will assist blood circulation and heat preservation.

The chemical constituents contained in the Simulated Bio-spectrum generator of the present invention have been described by way of examples. In practical use, the oxides can be substituted with fluorides, carbides, or nitrites. The mixture ratio of these constituents can also be readjusted, but at least one or a few of the elements in Table A or their compounds should be contained. When any one of the following elements or its compounds serves as the main constituent, it should account for no less than 10%: chromium, magnesium, selenium, germanium, zinc, copper, aluminum, strontium, cerium, yttrium, calcium, zirconium, molybdenum, silicon, iron, vanadium.

The simulated bio-frequency spectrum generator of the present invention can also contain the radiation source of a gray body or a near black body which consists of a plurality of ceramics, metals, or the combination of ceramics and metals.

The principle of determining the proportions of the above chemical constituents or determining radiation sources of the gray body or near black body mentioned above is that their spectrum should be as similar to the spectrum of the subject organism as possible. That is to say, the simulated bio-spectrum should overlap with the bio-spectrum; the more the overlap, the better. For complicated organisms such as human beings or animals, the spectrum to be simulated with the constituents in certain proportions should be as broad as possible. It is preferable to cover ultraviolet, visible light, infrared through millimeter waves, so that sufficient transitions of the molecules, atoms and electrons can be elicited simultaneously.

The applicants find that whatever the proportions of the elements may be, the key point is whether the spectral signal generated by the simulated bio-spectrum generator and the energy elicited by the electrons or excited molecules can be utilized to achieve biological effects of beneficial regulation.

The chemical elements that the present invention concerns include most of the elements of the 2nd, 3rd, 4th, and 5th periods of the Mendeleev periodical table, and the rare earth elements of the lanthanium and actinium series. Most of these elements are metal elements and are used in the form of oxides, fluorides, nitrides, sulfides, borides, or carbides, preferably oxides. To generate Simulated Bio-spectrum that best resemble the inherent bio-spectrum as shown in FIG. 2, for material 4 of FIG. 6, it is preferable to select one of the following elements or their compounds: Co,Cu,Mo,Li,Be,B,Mg,Al,Si,K,Ca,Ti,V,Cr,Mn,Fe,Ni,Zn, Ge,Sr, Zr,Nb,Ta,Hf,Se,Tn,W,Ge,Au,Y. Whenever any one of the following elements or their compounds is taken as the main constituent of the simulated bio-spectrum generating component, its content is preferable not less than 50%: Cr. Mg, Se, Ge, Zn, Cu. Mn, Al, Sr, Ce, Y, Ca, Zr, Ti, Co, Mo, Si, Fe, V.

Alternatively, shown in Table A are the chemical elements used in the method and apparatus according to the present invention for the purpose of simulating the chemical elements to emit a first radiation having a wavelength in range from about 0.2 μm to about 50 μm and a second radiation having a wavelength in range from about 7500 μm to about 100,000 μm, or to emit a first radiation having a wavelength in range from about 0.5 μm to about 25 μm and a second radiation having a wavelength in range from about 5400 μm to about 500,000 μm.

The chemical elements can be mixed into the raw material of plastics directly, into paints, dyes, enamels, or other coating materials which will be painted onto the surface of the plastic products. They can also be mixed into the textiles (cloth, artificial leather) to form a radiating surface membrane. The plastics or textiles which can radiate the Simulated Bio-spectrum can be used for health care of the human body or animals, for crop breeding or seedling nursing as well as for microbiologic fermentation.

TABLE A

Chemical elements used in the present invention

| Monomer | | Oxides | Carbides | Nitrides | Fluorides | Borides |
|---|---|---|---|---|---|---|
| Cobalt | Co | | | | | |
| Copper | Cu | | | | | |
| Molybdenum | Mo | | | | | |
| Lithium | Li | | | | | |
| Beryllium | Be | BeO | $Be_2C$ | $Be_3N_2$ | | |
| Boron | B | $B_2O_3$ | $B_4C$ | BN | | |
| Magnesium | Mg | MgO | | | $MgF_2$ | |
| Aluminum | Al | $Al_2O_3$ | | | | |
| Silicon | Si | $SiO_2$ | NbC | NbN | | |
| Potassium | K | KO | | | | |
| Calcium | Ca | CaO | | | | |
| Titanium | Ti | $TiO_2$ | TiC | TiN | | $TiB_2$ |
| Vanadium | V | $V_2O_5$ | VC | VN | | $VB_2$ |
| Chromium | Cr | | $Cr_3C_2$ | CrN | | $CrB(Cr_3B_4)$ |
| Manganese | Mn | $MnO_2$ | | | $MnF_2$ | |
| Iron | Fe | $Fe_2O_3$ | | | | |
| Nickel | Ni | NiO | | | | |
| Zinc | Zn | ZnO | | | $ZnF_2$ | |
| Germanium | Ge | GeO | | | | |
| Strontium | Sr | SrO | | | | |
| Zirconium | Zr | $ZrO_2$ | ZrC | ZrN | | $ZrB_2$ |
| Niobium | Nb | | NbC | NbN | | $NbB_2$ |
| Tantalum | Ta | | TaC | TaN | | $TaB_2$ |
| Hafnium | Hf | $HfO_2$ | HfC | HfN | | HfB |
| Selenium | Se | | | | | |
| Thorium | Tn | $TnO_2$ | TnC | TnN | | $TnB_4(TnB_6)$ |
| Tungsten | W | | $WcW_2C$ | | | WB |
| Cerium | Ce | $CeO_2$ | | | | |
| Gold | Au | | | | | |
| Yttrium | Y | $Y_2O_3$ | | | | |

In the case of application of the present invention, one or a plurality of elements and their compounds can be selected from Table A according to the specific living organism to be regulated or the requirements for the simulation or partial simulation of the Simulated Bio-spectrum.

Alternative mixture ratios of the elements used in the emitting layer of the simulated bio-spectrum generator, not necessarily preferred, will now be described:

EXAMPLE No. 1

The emitting layer of the Simulated Bo-spectrum generator contains 16 elements mainly in the form of oxides. The mixture ratio is: chromium oxide 95%, selenium oxide≧1%, chromium≧0.8%, germanium oxide≧0.8%, zinc oxide≧0.5%, ferric oxide≧0.5%, magnesium oxide≧0.1%, molybdenum oxide≧0.1%, strontium oxide≧0.1%, vanadium oxide≧0.1%, aluminum oxide≧0.1%, silicon oxide≧0.1%, lanthanium≧0.1%, magnesium fluoride≧0.1%.

EXAMPLE No. 2

The emitting layer of the Simulated Bio-spectrum generator contains:

| contains: | |
|---|---|
| chromium oxide 95% | ferric oxide ≧ 0.5% |
| chromium ≧ 0.8% | zinc oxide ≧ 0.4% |
| copper oxide ≧ 0.1% | cobalt oxide ≧ 0.1% |
| manganese oxide ≧ 0.1% | molybdenum oxide ≧ 0.1% |
| selenium oxide ≧ 0.7% | strontium oxide ≧ 0.1% |
| vanadium oxide ≧ 0.1% | aluminum oxide ≧ 0.1% |
| magnesium oxide ≧ 0.1% | silicon oxide ≧ 0.1% |
| germanium oxide ≧ 0.6% | lanthanium ≧ 0.1% |
| boric oxide ≧ 0.1% | magnesium fluoride ≧ 0.1% |

EXAMPLE No. 3

The emitting layer of the Simulated Bio-spectrum generator should include the following constituents:

| should include the following constituents: | |
|---|---|
| chromium oxide 93% | ferric oxide ≧ 0.5% |
| chromium ≧ 0.8% | zinc oxide ≧ 0.5% |
| copper oxide ≧ 0.1% | cobalt oxide ≧ 0.1% |
| manganese oxide ≧ 0.1% | molybdenum oxide ≧ 0.1% |
| selenium oxide ≧ 1% | strontium oxide ≧ 0.1% |
| vanadium oxide ≧ 0.1% | aluminum oxide ≧ 0.1% |
| magnesium oxide ≧ 0.1% | silicon oxide ≧ 0.1% |
| germanium fluoride ≧ 0.1% | lanthanium ≧ 0.1% |
| magnesium fluoride ≧ 0.1% | |

Elements like lithium, potassium, and titanium may also be added, but the content of each of the should not exceed 0.2%.

EXAMPLE No. 4

The emitting layer of the Simulated Bio-spectrum generator contains the following:

| | |
|---|---|
| chromium oxide 94% | ferric oxide ≧ 0.5% |
| chromium ≧ 0.8% | zinc oxide ≧ 0.7% |
| copper oxide ≧ 0.2% | cobalt oxide ≧ 0.2% |
| manganese oxide ≧ 0.3% | molybdenum oxide ≧ 0.1% |
| selenium oxide 0.9% | strontium oxide ≧ 0.1% |
| vanadium oxide ≧ 0.1% | aluminum oxide ≧ 0.1% |
| magnesium oxide ≧ 0.1% | silicon oxide ≧ 0.1% |
| germanium oxide ≧ 0.8% | lanthanium ≧ 0.1% |
| $CaCO_3$ ≧ 0.1% | |

EXAMPLE No. 5

The emitting layer of the Simulated Bio-spectrum generator contains the following:

contains the following:

| | |
|---|---|
| chromium oxide 94% | ferric oxide ≥ 0.5% |
| chromium ≥ 0.8% | zinc oxide ≥ 0.8% |
| copper oxide ≥ 0.2% | cobalt oxide ≥ 0.2% |
| manganese oxide ≥ 0.3% | molybdenum oxide ≥ 0.1% |
| selenium oxide ≥ 0.9% | strontium oxide ≥ 0.1% |
| vanadium oxide ≥ 0.1% | aluminum oxide ≥ 0.1% |
| magnesium oxide ≥ 0.1% | silicon oxide ≥ 0.1% |
| germanium oxide ≥ 0.8% | lanthanium ≥ 0.1% |
| KI ≥ 0.1% | $BO_2$ ≥ 0.1% |
| $CaCO_3$ ≥ 0.1% | $MgF_2$ ≥ 0.1% |

EXAMPLE No. 6

The emitting layer of the Simulated Bio-spectrum generator contains the following:

contains the following:

| | |
|---|---|
| chromium oxide 94% | ferric oxide ≥ 0.5% |
| chromium ≥ 0.8% | zinc oxide ≥ 0.5% |
| copper oxide ≥ 0.1% | cobalt oxide ≥ 0.1% |
| manganese oxide ≥ 0.1% | molybdenum oxide ≥ 0.1% |
| selenium oxide ≥ 0.9% | strontium oxide ≥ 0.1% |
| vanadium oxide ≥ 0.1% | aluminum oxide ≥ 0.1% |
| magnesium fluoride ≥ 0.1% | silicon oxide ≥ 0.1% |
| germanium oxide ≥ 0.8% | lanthanium oxide ≥ 0.1% | and a small amount of metal elements such as lithium, potassium, and sodium, their total amount should not exceed 0.5%.

EXAMPLE No. 7

The emitting layer of the Simulated Bio-spectrum generator contains the following:

| | |
|---|---|
| chromium oxide 95% | ferric oxide ≥ 0.5% |
| chromium ≥ 0.8% | zinc oxide ≥ 0.5% |
| copper oxide ≥ 0.1% | cobalt oxide ≥ 0.1% |
| manganese oxide ≥ 0.1% | molybdenum oxide ≥ 0.1% |
| selenium oxide ≥ 0.9% | strontium oxide ≥ 0.1% |
| vanadium oxide ≥ 0.1% | aluminum oxide ≥ 0.1% |
| magnesium oxide ≥ 0.2% | silicon oxide ≥ 0.1% |
| germanium oxide ≥ 0.8% | lanthanium ≥ 0.1% |

EXAMPLE No. 8

The emitting layer of the Simulated Bio-spectrum generator contains the following:

| | |
|---|---|
| chromium oxide 92% | ferric oxide ≥ 0.5% |
| chromium ≥ 0.8% | zinc oxide ≥ 0.7% |
| copper oxide ≥ 0.1% | cobalt oxide ≥ 0.1% |
| manganese oxide ≥ 0.2% | molybdenum oxide ≥ 1% |
| selenium oxide ≥ 1% | strontium oxide ≥ 0.1% |
| vanadium oxide ≥ 0.1% | silicon oxide ≥ 0.1% |
| magnesium oxide ≥ 0.1% | lanthanium ≥ 0.1% |
| KI ≥ 0.1% | |

Suitable amount (no more than 0.2%) of elements like titanium or boron are added.

EXAMPLE No. 9

The emitting layer of the Simulated Bio-spectrum generator contains the following:

contains the following:

| | |
|---|---|
| selenium oxide ≥ 5% | germanium oxide ≥ 5% |
| silicon oxide ≥ 50% | thorium oxide ≥ 4% |
| cerium oxide ≥ 5% | zirconium oxide ≥ 15% |
| boron nitride oxide ≥ 10% | titanium carbide ≥ 3% |
| tungsten carbide ≥ 3% | |

Beside, platinum 0.01% is added.

EXAMPLE No. 10

The emitting layer of the Simulated Bio-spectrum generator contains the following:

| | |
|---|---|
| aluminum oxide ≥ 85/5 | ferric oxide ≥ 3% |
| cobalt oxide ≥ 2% | titanium oxide ≥ 3% |
| silicon oxide ≥ 3% | hafnium oxide ≥ 2% |

Beside, platinum 0.01% is added.

EXAMPLE No. 11

The emitting layer of the Simulated Bio-spectrum generator contains the following:

| | |
|---|---|
| yttrium oxide ≥ 5% | FeCaMnFeOx ≥ 90% |
| silicon oxide ≥ 5% | |

EXAMPLE No. 12

The emitting layer of the Simulated Bio-spectrum generator contains the following:

| | |
|---|---|
| chromium oxide ≥ 96% | chromium ≥ 0.1% |
| zinc oxide ≥ 1% | silicon dioxide ≥ 1% |

EXAMPLE No. 13

The emitting layer of the Simulated Bio-spectrum generator contains the following:

| | |
|---|---|
| titanium oxide ≥ 90% | zirconium oxide ≥ 5% |
| silicon oxide ≥ 1% | ferric oxide ≥ 1.5% |
| zinc oxide ≥ 1% | copper oxide ≥ 1% |
| beryllium oxide ≥ 0.5% | |

EXAMPLE No. 14

The emitting layer of the Simulated Bio-spectrum generator contains the following:

| | |
|---|---|
| silicon carbide monomer (high purity) 90% | zinc oxide 1% |
| chromium 2% | |
| ferric oxide 1% | |

EXAMPLE No. 15

The emitting layer of the Simulated Bio-spectrum generator contains the following:

| | |
|---|---|
| silicon oxide ≧ 80% | ferric oxide ≧ 2% |
| vanadium oxide ≧ 2% | zinc oxide ≧ 2% |
| titanium oxide ≧ 2% | boron nitride ≧ 2% |
| tungsten carbide ≧ 1% | magnesium oxide ≧ 2% |
| calcium oxide ≧ 5% | cerium oxide ≧ 2% |

EXAMPLE No. 16

The emitting layer of the Simulated Bio-spectrum generator contains the following:

| | |
|---|---|
| aluminum oxide ≧ 85% | cerium oxide ≧ 1% |
| ferric oxide ≧ 5% | cobalt oxide ≧ 3% |
| chromium oxide ≧ 5% | silicon oxide ≧ 1% |
| cerium oxide ≧ 2% | |

EXAMPLE No. 17

Where the range of the spectrum is restricted to 0.5–30 μm, the Simulated Bio-spectrum generator contains magnesium fluoride ($MgF_2$) in 100%.

EXAMPLE No. 18

The selective material emitting the Simulated Bio-spectrum can also be made to contain mainly magnesium fluoride (50%), and the other constituents can be materials with high chromaticity, high rate or radiation, and broad comprehensive spectrum. In this Example 18, they are:

| | |
|---|---|
| magnesium fluoride ($MgF_2$) ≧ 50% | titanium oxide ($TiO_2$) ≧ 5% |
| nickel oxide (NiO) ≧ 5% | tin oxide ($SnO_2$) ≧ 1% |
| manganese oxide ($MnO_2$) ≧ 6% | (BN) ≧ 20% |

Also, where Simulated Bio-spectrum is generated using a power source, such as electricity that can be intermittently operated, the Simulated Bio-spectrum can be generated intermittently with an intermittently operated power source which works, for example, two seconds in every 10 seconds, so that a changing spectrum is generated.

EXAMPLE No. 19

The emitting layer of the Simulated Bio-spectrum generator contains the following:

| | |
|---|---|
| chromium oxide ≧ 90% | ferric oxide ≧ 1% |
| chromium ≧ 1% | zinc oxide ≧ 1% |
| copper oxide ≧ 0.2% | cobalt oxide ≧ 0.2% |
| manganese oxide ≧ 0.5% | molybdenum oxide ≧ 0.1% |
| selenium oxide ≧ 1.5% | strontium oxide ≧ 0.1% |
| vanadium oxide ≧ 0.1% | aluminum oxide ≧ 0.1% |
| vanadium oxide ≧ 0.1% | aluminum oxide ≧ 0.2% |
| magnesium oxide ≧ 0.8% | silicon oxide ≧ 0.3% |
| germanium oxide ≧ 1% | lanthanium ≧ 0.1% |
| KI ≧ 0.1% | |

EXAMPLE No. 20

The emitting layer of the Simulated Bio-spectrum generator contains the following:

| | |
|---|---|
| chromium oxide ≧ 80% | beryllium oxide ≧ 1% |
| copper oxide ≧ 2% | zinc oxide ≧ 3% |
| cobalt oxide ≧ 2% | niobium oxide ≧ 1% |
| calcium oxide ≧ 3% | strontium oxide ≧ 1% |
| silicon oxide ≧ 2% | selenium oxide ≧ 2% |
| molybdenum oxide ≧ 1% | ferric oxide ≧ 2% |

EXAMPLE No. 21

The emitting layer of the Simulated Bio-spectrum generator contains the following:

| | |
|---|---|
| zinc oxide ≧ 5% | ferric oxide ≧ 3% |
| silicon ≧ 5% | germanium oxide ≧ 10% |
| thorium oxide ≧ 2% | chromium oxide ≧ 75% |

Figures 1, 7A:
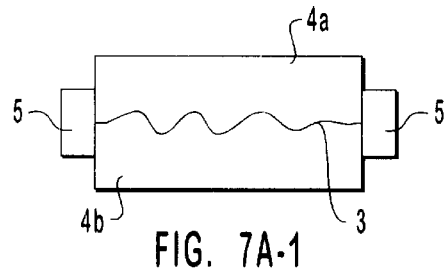
Figures 2, 7A:
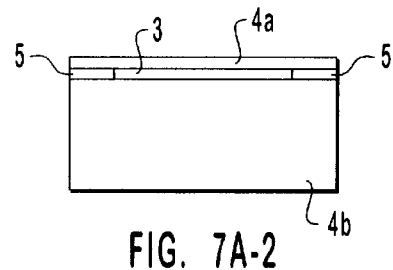

FIGS. 7A-1, 7A-2, 7B-1, 7B-2, 7C-1, 7C-2 and 7D diagrammatically illustrate embodiments of a body through which energy is propagated to stimulate a material incorporated therein so as to emit from said material a predetermined radiation. Here the body is referred to as a simulated biospectrum generator. In FIG. 7A-1, body 4 comprises a substrate 4B and an emitting layer 4A disposed on substrate 4B and composed of borides, nitrides, carbides, sulfides or fluoride. 5 is the electrode. The proportions of these elements and their compounds are determined by the kind of organism to be regulated and its status of growth.

Material of substrate 4B is selected according to the type of energy source which is an electric power source in this embodiment. Substrate 4B can be made from non-metal materials, such as ceramics with low hygroscopic properties, high heat resistance, high mechanical strength, high radiance, or heat resistant (<150° C.) plastics with high radiance or quartz glass, micro crystal glass or other kinds of glass with high heat resistance and high strength. It can also be made from electric materials such as carbon rod or resistors which have high electric conductivity and are capable of reaching heat producing temperatures; Various kinds of chemical elements and their compounds are mixed in the right proportion, and then diluted into liquid adhesive, or they may be made into coating material or enamel pulp and coated onto the surface of the substrate to form the emitting layer. Energy transducer 3 can be an electric heating wire or the like which is embedded into the substrate as shown or disposed on the ends of the substrate to convert electric energy into thermal energy. The heat generated by the heating wire is used to excite the chemical elements in the emitting layer. The temperature should not be lower than the body temperature of the living organisms. An electrical power can be supplied by a battery.

The heating wire 3 in FIG. 7A-1 can be replaced by a layer of conducting membrane 3 (FIG. 7A-2) formed on the surface of the substrate 4B by means of metal oxidation techniques (high temperature hydrolysis of chlorides to form a conducting membrane of metal-oxides) to make the body more solidified thus increasing the speed and efficiency with which the electric energy is converted into thermal energy (FIG. 7A-1). In FIG. 7A-2, the emitting layer 4A is coated on the surface of the conducting membrane.

FIG. 7B-1 is another embodiment of the simulated bio-spectrum generator according to the present invention. In this embodiment, substrate 4B is integrated with the energy transducer 3 in a manner that a conducting substance is infiltrated into non-metal material to make it electrically conductive and have satisfactory resistance. The emitting layer 4A is then coated onto 4B substrate to form a Simulated Bio-spectrum generator. The substrate can also be made from metals. In this case, electric current introduced into the substrate is converted into thermal energy and the substrate acts as the energy transducer at the same time. Then a layer of enamel pulp mingled with one or more chemical elements and their compounds in the right proportion is coated onto the metal substrate and sintered under high temperature to form a Simulated Bio-spectrum generator of metal substrate.

Figures 1, 7B:
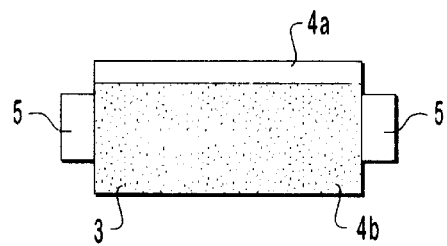
Figures 2, 7B:
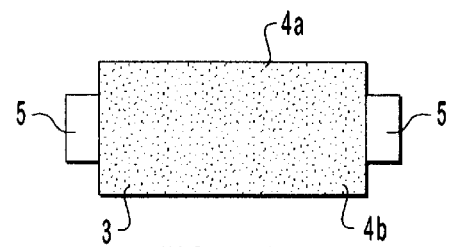

In FIG. 7B-2, the chemical elements and their compounds constituting the emitting layer 4A can also be doped into substrate 4B and then sintered under high temperature to form a Simulated Bio-spectrum generator (FIG. 7B-2) which is even more integral than that of FIG. 7B-1 as shown in FIG. 7B-2.

Figures 1, 7C:
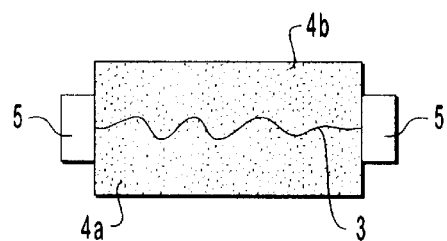
Figures 2, 7C:
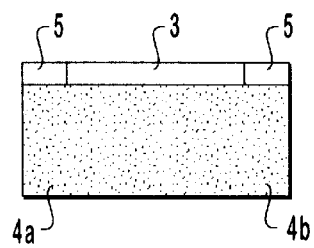

FIG. 7C-1 is still another embodiment of the simulated bio-spectrum generator according to the present invention. In this embodiment, one or more chemical elements and their compounds are mixed-in the right proportion with pot clay and sintered into an integral body so that the substrate per se contains the constituents that generate the simulated bio-spectrum. When an energy transducer such as an electric heating wire is embedded into the substrate, an integrated simulated bio-spectrum generator is formed.

In FIG. 7C-2, a conducting membrane 3 can be plated onto the surface of the substrate 4B containing the chemical elements of the emitting layer 4A. The conducting membrane 3 replaces the heating wire 3, and makes the Simulated Bio-spectrum generator a more integral body as shown in FIG. 7C-2.

Figure 7D:
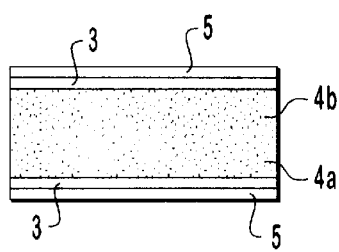

FIG. 7D is still another embodiment of the simulated bio-spectrum generator according to the present invention. In this embodiment, temperature resisting glass is used as the material of the substrate and one or more chemical elements and their compounds are mixed in the right proportion into the raw glass during sintering. A special glass body containing the constituents that generate the Simulated Bio-spectrum is formed by sintering. Then a layer of semiconductor membrane is formed on the surface of the glass as the energy transducer by means of the metal oxidation, thus forming a colorless and transparent Simulated Bio-spectrum generator. In this embodiment, the material of the substrate can also be pot clay containing one or more chemical elements and their compounds so that the substrate per se contains constituents that generate the Simulated Bio-spectrum. An integrated solid ceramic simulated bio-spectrum generator is formed by disposing a layer of conducting membrane of metal oxides on the surface of such a substrate as an electrically conducting energy transducer.

The substrate can be made from either permanent or ferromagnetic materials. In this case, the emitting layer is plated onto the magnetic substrate and a non-thermal Simulated Bio-spectrum generator made from magnetic material is formed.

FIGS. 7A-1, 7A-2, 7B-1, 7B-2, 7C-1, 7C-2 and 7D are particularly designed to stimulate emitting layer 4A disposed on substrate 4B with electrical or magnetic energy. It is contemplated that heat from the human body is also an energy source that can stimulate a selected material of the compositions described above so as to emit a first radiation having a wavelength in range from about 0.2 $\mu$m to about 50 $\mu$m and a second radiation having a wavelength in range from about 7500 $\mu$m to about 100,000 $\mu$m, although the amount of such radiation will not be as great as could be emitted by electrical power sources. Nevertheless, the radiation emission principles depicted in FIG. 6 apply in the case of fabric heated by human body heat, where the body heat stimulates a material in the fabric to emit the Simulated Bio-spectrum.

FIGS. 8A, 8B, 9A, 9B, 10A, 10B, 11A, 11B, 11C, and 11D show apparel made from fabric structures having a material incorporated therein which, when stimulated by energy, produces the Simulated Bio-spectrum. Like reference numerals depict like structures. Any of the depicted fabric structures can be made of a fiber having a substrate surface with a radiation generating material thereon. The radiation generation material, when stimulated by energy, emits a predetermined spectrum having a first electromagnetic radiation having a wavelength range selected from the group consisting of about 0.2 $\mu$m to about 50 $\mu$m, and about 0.4 $\mu$m to about 25 $\mu$m, and a second radiation having a wavelength range selected from the group consisting of about 7500 $\mu$m to about 100,000 $\mu$m, and about 5400 $\mu$m to about 500,000 $\mu$m.

Figure 8A:
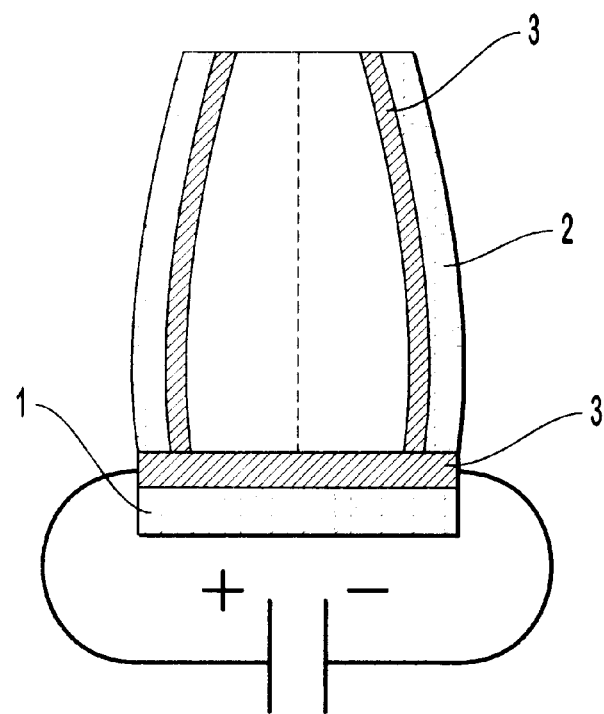
FIGS. 8A and 8B depict examples of a fabric having a material thereon which conserves body heat, and when the material is stimulated by energy, the material emits a predetermined radiation.
Figure 8B:
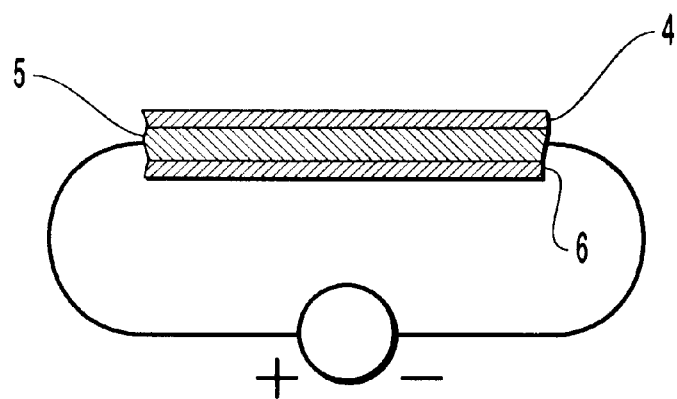

In FIG. 8A, which depicts a fabric from which a shoe is made, there is an equipping of a frequency-spectrum generation lining 3 in the interior surface of the regular sole 1 and upper 2. The structure of frequency-spectrum generation lining 3 is: paint frequency-spectrum generation layer 5 on the back side of fiber 4, equip a reflection layer 6 on the surface of frequency-spectrum generation layer 5, connect reflection layer 6 on the interior surface of sole 1 and upper, with glue or by sewing as in FIG. 8A. Next, add the chemical element substances which can produce the Simulated Bio-spectrum in the glue, apply the glue on sole 1 and/or in the interior surface of upper 2.

In FIGS. 9A and 9B, there is an addition of a frequency-spectrum generation lining as an interior lining in jackets and overcoats which have body heat conservation requirements. The structure is: add frequency-spectrum generation lining 3 as an interior lining in the inside surface of the outer cloth of jacket 7; reflection layer 6 is used as an interior surface.

In FIGS. 10A and 10B, a frequency-spectrum generation lining 3 equipped with reflection layer 6 may be adopted directly to make underwear, underpants, gloves, blankets, towels and other similar products.

Figure 11A:
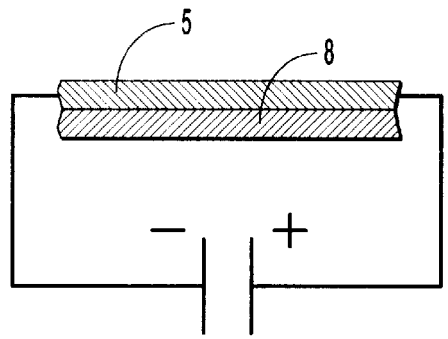
FIG. 11A through 11D are examples of a fabric having a material incorporated therein that conserves body heat, and when that material is stimulated by energy, the material emits a predetermined radiation.

In FIG. 11A, the original material of frequency-spectrum generation lining 3 can be made by painting a frequency-spectrum generation layer 5 on the surface of ordinary cotton or chemical fibers 8, which can be used as an interior lining of shoes and clothes, or be produced directly into shoes, clothes and similar products.

Figure 11B:
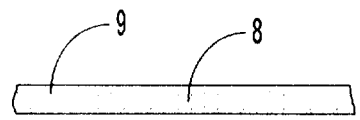

In FIG. 11B, mixed chemical element substances 9 of a frequency-spectrum generation layer the (particle of the chemical should be smaller than the diameter of the fiber) are in the fiber. Frequency-spectrum generation lining 3's original material is produced by making the fiber into clothes. It can be used as the interior lining of shoes, clothes, or be produced into shoes and clothes directly.

Figure 11C:
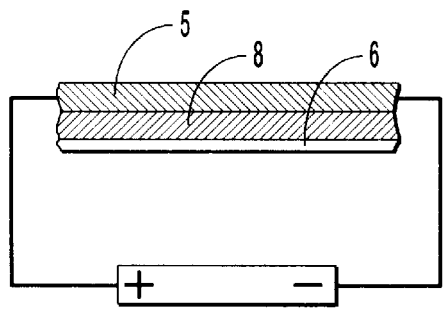
Figure 11D:
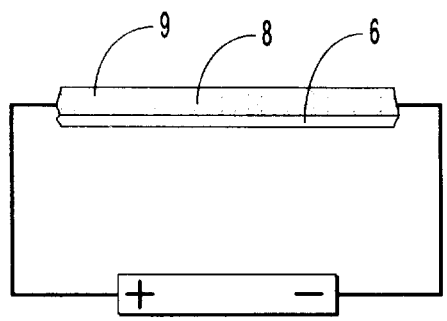

In FIG. 11C, in order to raise the efficiency of radiation, an aluminium reflection layer is equipped and glued on the surface of the frequency-spectrum generation line where a frequency-spectrum generation layer is painted, or to equip a reflection layer on any surface of the frequency-spectrum generation lining which is made up of cloth fiber with chemical element substances therein as seen in FIG. 11D where the reflection layer has no air pores. The reflection layer may comprise aluminium, tin, copper or other materials which have a good reflection nature.

The material of the frequency-spectrum generation layer may refer to the recipe for a system of simulated frequency-spectrum generation layer paint made known by the inventors, or a recipe of an ultrared paint recommended by publicized documents, or use of chemical substances including oxidates, and carbonates with a radiation nature.

Figure 12:
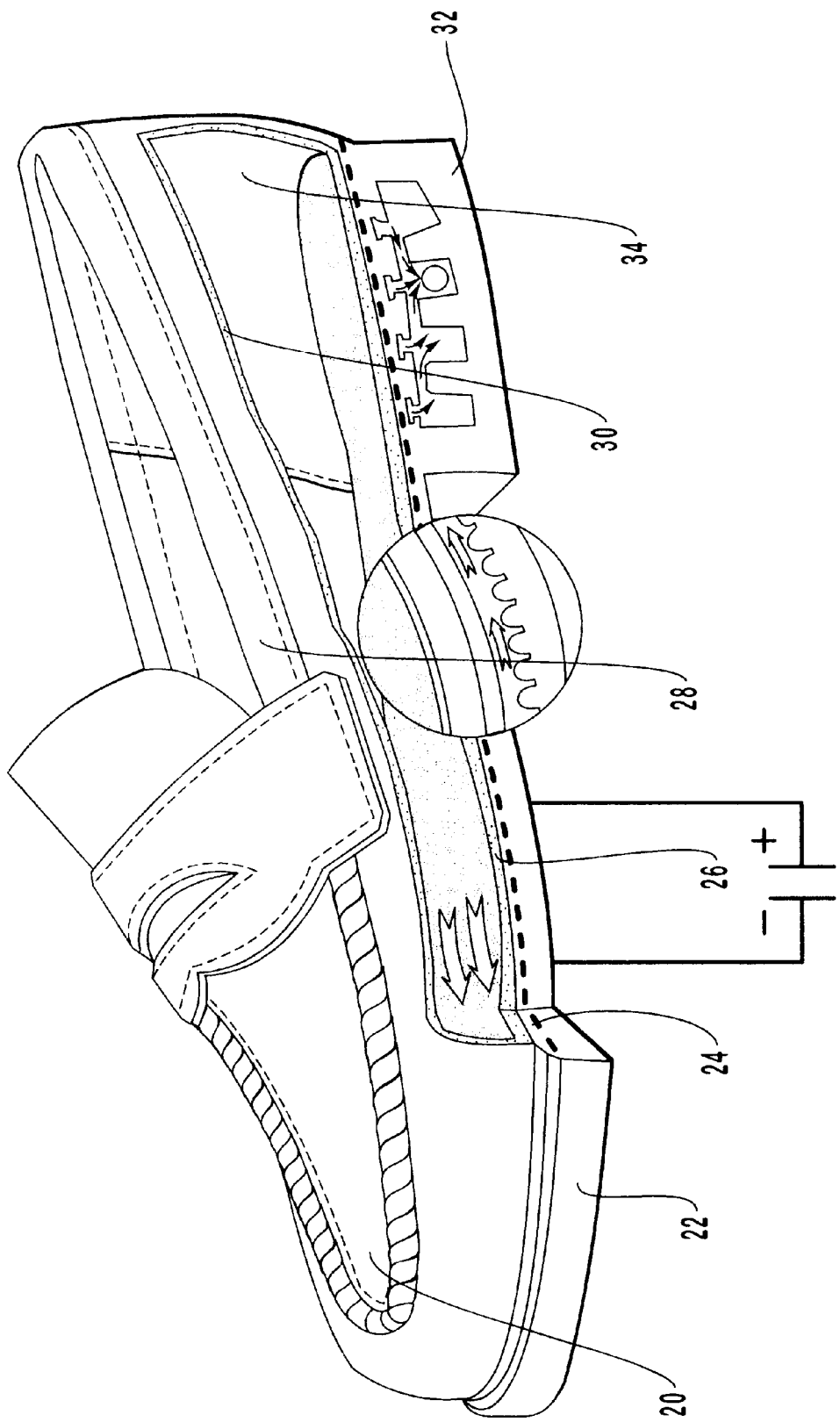
FIG. 12 depicts a shoe having a lining therein, the fabric lining having a material incorporated therein that conserves body heat, and when that material is stimulated by energy, the material emits a predetermined radiation.

FIG. 12 shows a shoe having a vamp 20, a sole 22, a shank 24, an insole 26, a shoe opening 28, several structures 30 composed of a radiation generating material, an air outlet 32, and a sock lining 34. The material of which structure 30 is composed is such that when stimulated by energy, the material emits an electromagnetic radiation that is similar to that created by the human body, namely a first radiation having a wavelength in range from about 0.2 $\mu$m to about 50 $\mu$m and a second radiation having a wavelength in range from about 7500 $\mu$m to about 100,000 $\mu$m. Alternatively, the two radiation wavelengths can also be in range from about 0.4 $\mu$m to about 25 $\mu$m and in range from about 5400 $\mu$m to about 500,000 $\mu$m.

FIGS. 9B, 10B, 11A, and 12 show an electrical power supply in electrical communication with a material on a fabric of a clothing article which, when stimulated by electrical energy from the electrical power supply, produces from the Simulated Bio-spectrum. FIGS. 11C and 11D illustrate the Simulated Bio-spectrum produced from a magnetic energy supply. A wearer's body heat, with or without the electrical or magnetic energy supply, will produce the Simulated Bio-spectrum.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A fabric comprising:

a plurality of fibers; and a material held in contact with said plurality of fibers that emits a predetermined spectrum when stimulated by energy, said predetermined spectrum including a first electromagnetic radiation that extends over a wavelength range from about 0.2 $\mu$m to about 50 $\mu$m, and including a second electromagnetic radiation that extends over a wavelength range from about 7500 $\mu$m to about 100,000 $\mu$m.

2. The fabric as defined in claim 1, wherein the predetermined spectrum has substantially no electromagnetic radiation that extends over a wavelength range from about 50 $\mu$m to about 7500 $\mu$m when the material is stimulated by energy.

3. The fabric as defined in claim 1, wherein the material is in communication with an energy supply source.

4. The fabric as defined in claim 3, wherein the energy supply source is an electrical power supply.

5. The fabric as defined in claim 1, wherein the first electromagnetic radiation is at least ninety percent of the electromagnetic radiation emitted by the material when stimulated by energy.

6. The fabric as defined in claim 1, wherein the material is substantially composed of a composition of which at least 10% thereof is an element selected from a group consisting of: Cr, Mg, Se, Ge, Zn, Cu, Mn, Al, Sr, Ce, Y, Ca, Zr, Ti, Co, Mo, Si, Fe, and V.

7. The fabric as defined in claim 1, wherein:

the first electromagnetic radiation is at least ninety percent of the electromagnetic radiation emitted by the material when stimulated by energy;

the second electromagnetic radiation is greater than zero percent but less than ten percent of the electromagnetic radiation emitted by the material when stimulated by energy; and the material emits substantially no electromagnetic radiation that extends over a wavelength range from about 50 $\mu$m to about 7500 $\mu$m when the material is stimulated by energy.

8. A fabric comprising:

a plurality of fibers; and a material held in contact with said plurality of fibers that emits a predetermined spectrum when stimulated by energy, said predetermined spectrum including a first radiation that extends over a wavelength range from about 0.4 $\mu$m to about 25 $\mu$m and a second radiation that extends over a wavelength range from about 5400 $\mu$m to about 500,000 $\mu$m.

9. The fabric as defined in claim 8, wherein the material emits substantially no electromagnetic radiation that extends over a wavelength range from about 25 $\mu$m to about 5400 $\mu$m when the material is stimulated by energy.

10. The fabric as defined in claim 8, wherein the material is in communication with an energy supply source.

11. The fabric as defined in claim 10, wherein the energy supply source is an electrical power supply.

12. The fabric as defined in claim 8, wherein the first electromagnetic radiation is at least ninety percent of the electromagnetic radiation emitted by the material when stimulated by energy.

13. The fabric as defined in claim 8, wherein the material is substantially composed of a composition of which at least 10% thereof is an element selected from a group consisting of: Cr, Mg, Se, Ge, Zn, Cu, Mn, Al, Sr, Ce, Y, Ca, Zr, Ti, Co, Mo, Si, Fe, and V.

14. The fabric as defined in claim 8, wherein:

the first electromagnetic radiation is at least ninety percent of the electromagnetic radiation emitted by the material when stimulated by energy;

the second electromagnetic radiation is greater than zero percent but less than ten percent of the electromagnetic radiation emitted by the material when stimulated by energy; and the material emits substantially no electromagnetic radiation that extends over a wavelength range from about 25 $\mu$m to about 5400 $\mu$m when the material is stimulated by energy.

15. A shoe comprising:

a sole, an insole, a shoe opening; and a lining situated between the sole and the shoe opening and having incorporated therein a material that when stimulated by energy emits a predetermined spectrum having:

a first electromagnetic radiation extending in a wavelength range selected from the group consisting of about 0.2 $\mu$m to about 50 $\mu$m, and about 0.4 $\mu$m to about 25 $\mu$m;

a second radiation extending in a wavelength range selected from the group consisting of about 7500 $\mu$m to about 100,000 $\mu$m, and about 5400 $\mu$m to about 500,000 $\mu$m.

16. The shoe as defined in claim 15, wherein the predetermined spectrum has substantially no electromagnetic radiation extending in a wavelength range selected from the group consisting of about 50 μm to about 7500 μm, and about 25 μm to about 5400 μm.

17. The shoe as defined in claim 15, wherein the material is in communication with an energy supply source.

18. The shoe as defined in claim 17, wherein the energy supply source is an electrical power supply.

19. The shoe as defined in claim 15, wherein the first electromagnetic radiation is at least ninety percent of the electromagnetic radiation emitted by the material when stimulated by energy.

20. The shoe as defined in claim 15, wherein the material is substantially composed of a composition of which at least 10% thereof is an element selected from a group consisting of: Cr, Mg, Se, Ge, Zn, Cu, Mn, Al, Sr, Ce, Y, Ca, Zr, Ti, Co, Mo, Si, Fe, and V.

21. The shoe as defined in claim 15, wherein:
the first electromagnetic radiation is at least ninety percent of the electromagnetic radiation emitted by the material when stimulated by energy;
the second electromagnetic radiation is greater than zero percent but less than ten percent of the electromagnetic radiation emitted by the material when stimulated by energy; and
the predetermined spectrum has substantially no electromagnetic radiation extending in a wavelength range selected from the group consisting of about 50 μm to about 7500 μm, and about 25 μm to about 5400 μm.

22. The shoe as defined in claim 15, wherein the material is coated on the lining.

23. The shoe as defined in claim 15, wherein the material is adjacent to at least one of the sole and insole.

24. The shoe as defined in claim 15, further comprising a layer for reflecting body heat.

25. The shoe as defined in claim 24, wherein the layer for reflecting body heat is composed of a metal.

26. A fiber comprising:
a substrate surface; and
a material on said substrate surface that when stimulated by energy emits a predetermined spectrum having:
a first electromagnetic radiation extending in a wavelength range selected from the group consisting of about 0.2 μm to about 50 μm, and about 0.4 μm to about 25 μm;
a second radiation extending in a wavelength range selected from the group consisting of about 7500 μm to about 100,000 μm, and about 5400 μm to about 500,000 μm.

* * * * *

UNITED STATES PATENT AND TRADEMARK OFFICE
CERTIFICATE OF CORRECTION

PATENT NO. : 6,120,531
DATED : September 19, 2000
INVENTOR(S) : Lin Zhou; Xue-Shan Zhang It is certified that error appears in the above-identified patent and that said Letters Patent is hereby corrected as shown below:

Title page,
Item [73], delete "Assignee: Micron, Technology, Boise, Id." and insert -- Assignee: None --

Column 1,
Line 52, after "heat lamp" insert a period
Line 53, after "from about" change "0.0.5" to -- 0.5 --

Column 3,
Line 24, after "dotted and dashed" insert -- line showing --
Line 37, delete the comma after "emitted"

Column 6,
Line 46, before "infrared through" insert -- and --

Column 7,
Line 66, after "Simulated" change "Bo-spectrum" to -- Bio-spectrum --

Column 8,
Line 45, before "should not exceed" delete -- of the --

Column 12,
Line 42, after "heat producing" change "temperatures;" to -- temperatures. --
Line 49, before "or disposed" change "as shown" to -- (as shown) --

Column 13,
Line 3, after "coated onto" change "4B substrate" to -- substrate 4B --

UNITED STATES PATENT AND TRADEMARK OFFICE
CERTIFICATE OF CORRECTION

PATENT NO. : 6,120,531
DATED : September 19, 2000
INVENTOR(S) : Lin Zhou;

It is certified that error appears in the above-identified patent and that said Letters Patent is hereby corrected as shown below:

Column 13,
Line 17, insert a comma after "FIG. 7B-1"

Column 14,
Line 35, "generation lining" insert -- 3 --
Line 52, after "generation layer" change "the (particle" to -- (the particle --

Signed and Sealed this

Thirteenth Day of November, 2001

Attest:

NICHOLAS P. GODICI
Attesting Officer     Acting Director of the United States Patent and Trademark Office